US 9,510,952 B2

(12) United States Patent
Muir et al.

(10) Patent No.: US 9,510,952 B2
(45) Date of Patent: Dec. 6, 2016

(54) GLENOID TRIAL AND IMPLANT ASSEMBLY FOR REVERSE TOTAL SHOULDER ARTHROPLASTY AND METHOD OF USE

(71) Applicant: Biomet Manufacturing, LLC, Warsaw, IN (US)

(72) Inventors: Nicholas Muir, Winona Lake, IN (US); Bryce Isch, Warsaw, IN (US); Nathan Winslow, Warsaw, IN (US)

(73) Assignee: Biomet Maufacturing, LLC, Warsaw, IN (US)

( * ) Notice: Subject to any disclaimer, the term of this patent is extended or adjusted under 35 U.S.C. 154(b) by 30 days.

(21) Appl. No.: 14/678,032

(22) Filed: Apr. 3, 2015

(65) Prior Publication Data

US 2016/0287401 A1    Oct. 6, 2016

(51) Int. Cl.
*A61F 2/40*      (2006.01)
*A61F 2/30*      (2006.01)

(52) U.S. Cl.
CPC .............. *A61F 2/4081* (2013.01); *A61F 2/40* (2013.01); *A61F 2/4014* (2013.01); *A61F 2/4059* (2013.01); *A61F 2002/30329* (2013.01); *A61F 2002/30649* (2013.01); *A61F 2002/30672* (2013.01); *A61F 2002/4085* (2013.01); *A61F 2250/006* (2013.01)

(58) Field of Classification Search
CPC ...... A61F 2/4059; A61F 2/4081; A61F 2/40; A61F 2/4014; A61F 2002/4062; A61F 2002/4085; A61F 2002/4011; A61F 2002/30001; A61F 2002/30329; A61F 2002/30649; A61F 2002/30672; A61F 2002/4037; A61F 2002/404
USPC .......................................... 623/19.11–19.13
See application file for complete search history.

(56) References Cited

U.S. PATENT DOCUMENTS

| 6,589,248 | B1 | 7/2003 | Hughes |
| 2003/0187510 | A1 | 10/2003 | Hyde |
| 2009/0216332 | A1 | 8/2009 | Splieth et al. |
| 2010/0049327 | A1* | 2/2010 | Isch .................. A61F 2/34 623/19.12 |
| 2013/0150975 | A1 | 6/2013 | Iannotti et al. |
| 2013/0197650 | A1 | 8/2013 | Smits et al. |

FOREIGN PATENT DOCUMENTS

DE              320756 C     4/1920

OTHER PUBLICATIONS

STIC search results (ProQuest NPL).*

(Continued)

*Primary Examiner* — David Isabella
*Assistant Examiner* — Dinah Baria
(74) *Attorney, Agent, or Firm* — Schwegman Lundberg & Woessner, P.A.

(57) ABSTRACT

A glenoid trial and implant assembly for use in reverse total shoulder arthroplasty is provided along with a method for using the same. The glenoid trial and implant assembly includes a baseplate assembly, an adapter assembly, a glenoid trial, a glenoid implant, a humeral cup, and a positioning guide. The glenoid trial is coupled to the adapter assembly when the glenoid trial and implant assembly is assembled in a trialing configuration. The glenoid implant is coupled to the adapter assembly when the glenoid trial and implant assembly is assembled in an installed configuration. A temporary connection, which may be magnetic, releasably couples the glenoid trial to the adapter assembly and provides separation of the glenoid trial and the adapter assembly without requiring disassembly of the adapter assembly. A permanent connection fixes the glenoid implant to the adapter assembly.

19 Claims, 9 Drawing Sheets

(56) References Cited

OTHER PUBLICATIONS

STIC search results (ProQuest Patents).*
International Application Serial No. PCT/US2016/023563, International Search Report mailed Aug. 4, 2016, 8 pgs.
International Application Serial No. PCT/US2016/023563, Written Opinion mailed Aug. 4, 2016, 8 pgs.

* cited by examiner

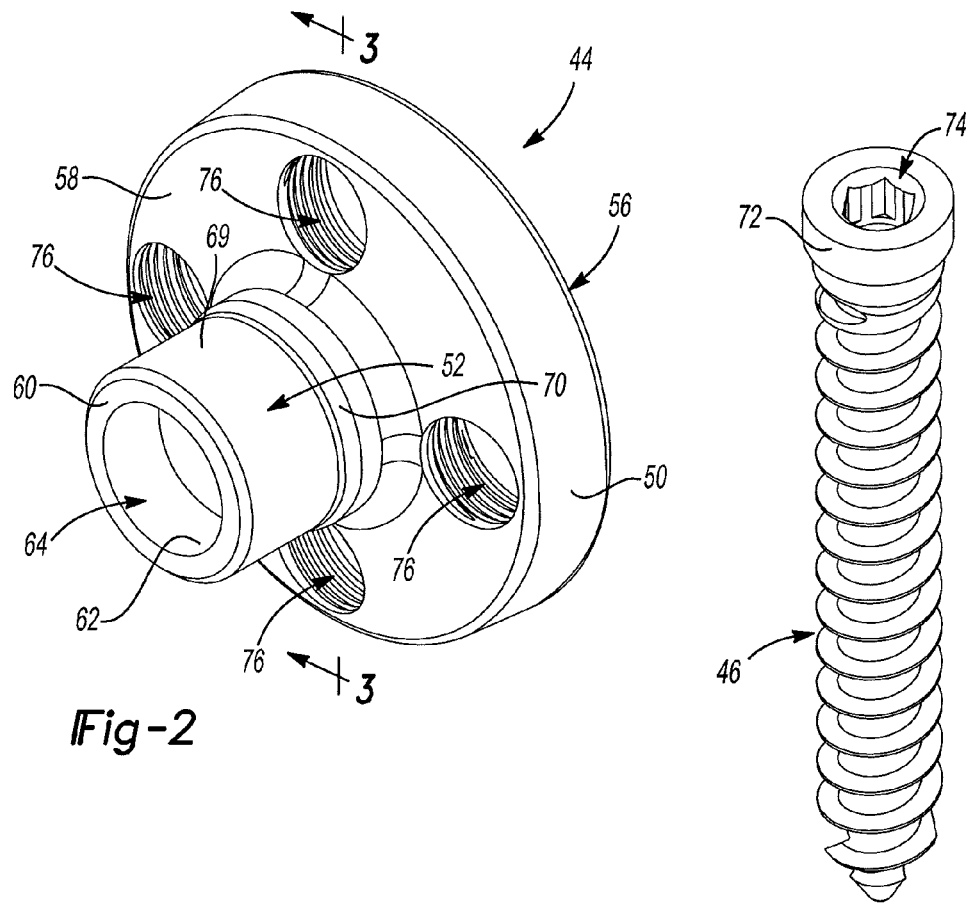
Fig-2
Fig-4
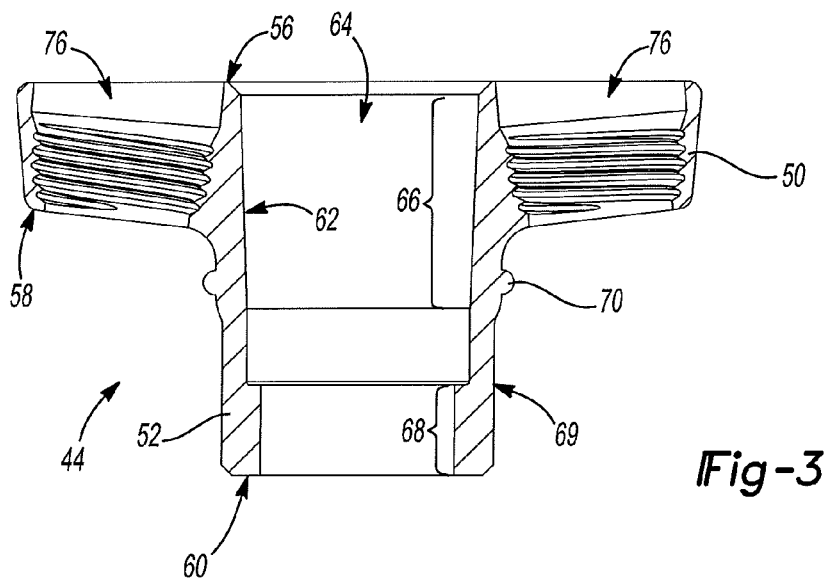
Fig-3

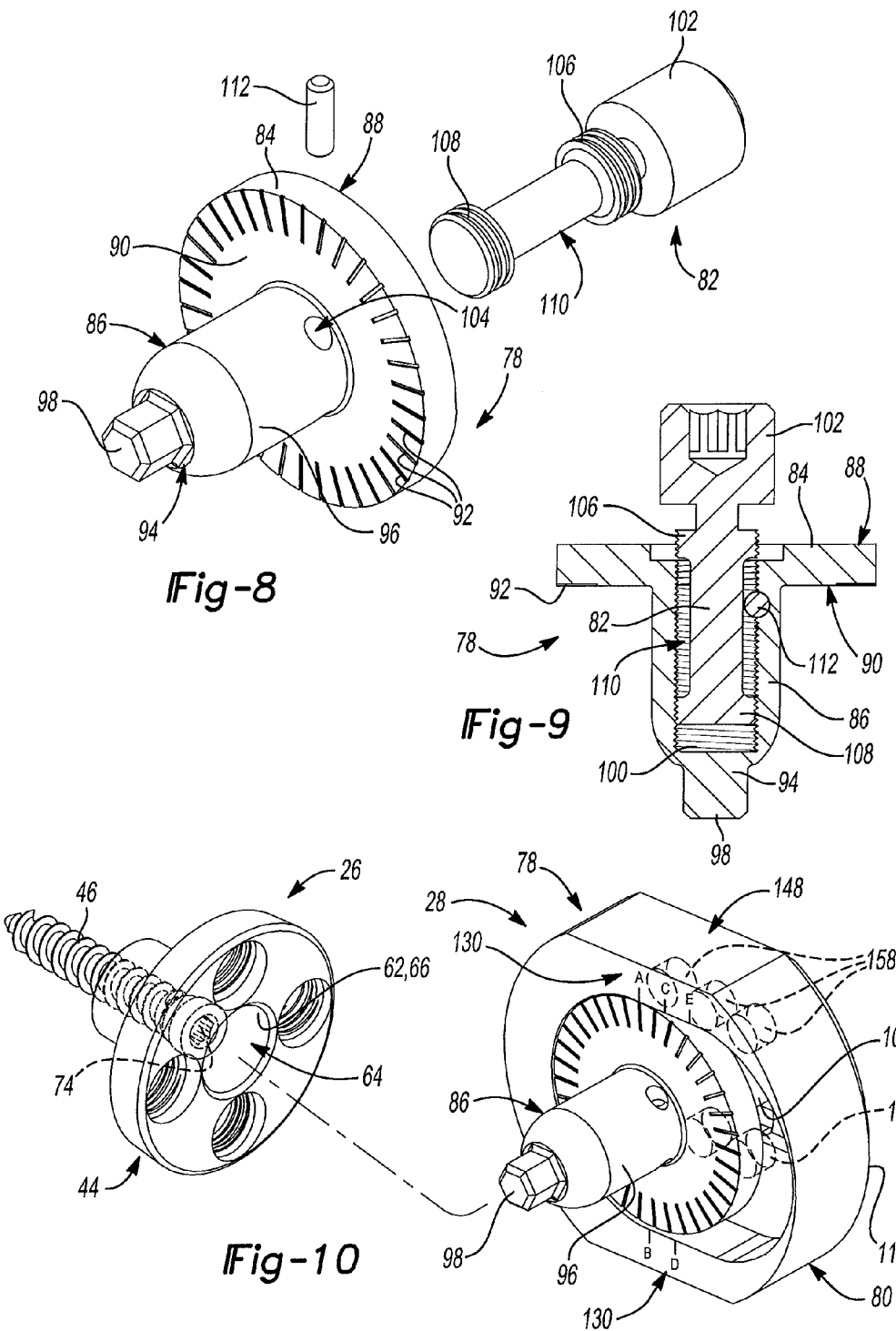

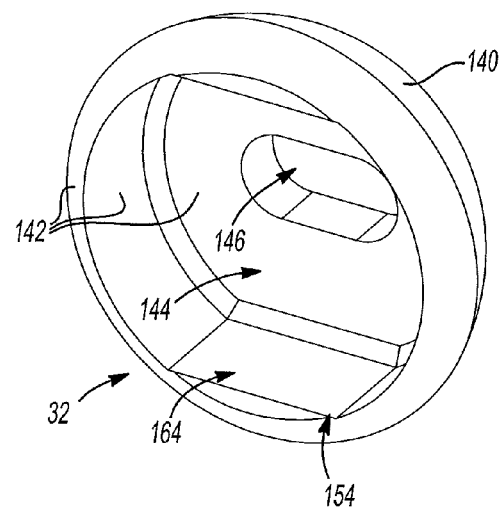
Fig-17
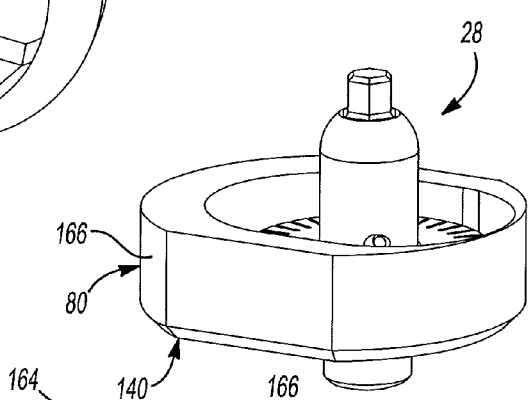
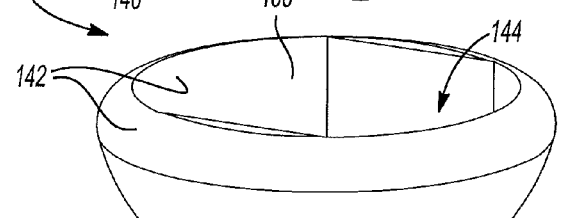
Fig-18
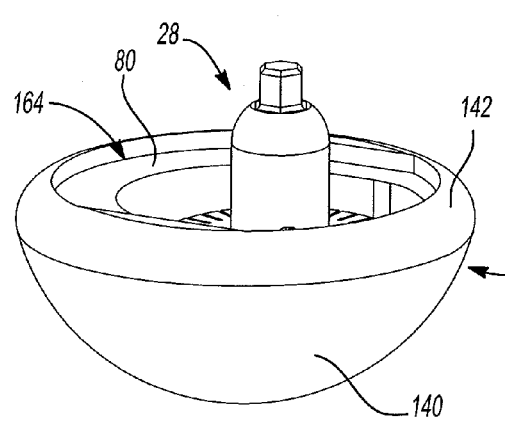
Fig-19

GLENOID TRIAL AND IMPLANT ASSEMBLY FOR REVERSE TOTAL SHOULDER ARTHROPLASTY AND METHOD OF USE

FIELD

The subject disclosure relates to the field of glenoid trial and implant assemblies for use in total shoulder arthroplasty. More particularly, the subject disclosure relates to reverse total shoulder arthroplasty where the humeral trial and implant assembly is not anatomically correct. Such humeral trial and implant assemblies are surgically implanted into the shoulder of a patient between the humerus and the glenoid.

BACKGROUND

This section provides background information related to the present disclosure which is not necessarily prior art.

Reverse total shoulder arthroplasty is one of several types of shoulder replacement surgeries. In reverse total shoulder arthroplasty, a portion of a patient's humerus and a portion of the patient's glenoid is replaced and/or augmented with implantable components. These components may include a humeral cup and a glenoid implant. Generally, the humeral cup is coupled to the humerus, replacing the head of the humerus, and the glenoid implant is installed on the glenoid. In an anatomically correct shoulder joint, the "ball" of the shoulder joint is on the humerus side of the shoulder joint. Because the glenoid implant acts as the "ball" and the humeral cup acts as the glenoid, in reverse total shoulder arthroplasty, the "ball" is on the glenoid side of the shoulder joint. In other words, the relationship between the components in the surgically created shoulder joint is opposite that of the anatomically correct shoulder joint.

Because anatomy varies among patients, a surgeon must choose a glenoid implant that fits the patient undergoing surgery. To determine proper fit, a glenoid trial is used. Before the glenoid implant is installed, the surgeon positions the glenoid trial on a baseplate assembly that is installed on the glenoid. An adapter assembly may be used to couple the glenoid trial to the baseplate assembly where a threaded fastener attaches the glenoid trial to the adapter assembly. An apical opening is provided in the glenoid trial to receive the threaded fastener and to provide access to the head of the threaded fastener. Once the glenoid trial is installed on the adapter assembly and is positioned on the baseplate assembly, the surgeon trials the surgically created shoulder joint by moving the humerus through a range of motion. Such trialing allows the surgeon to evaluate the fit and function of the glenoid trial. If trialing is unsatisfactory, the surgeon must remove the glenoid trial from the baseplate assembly and repeat the process with another glenoid trial that has a different size and/or shape. This process continues until a satisfactory glenoid trial is found.

Once a satisfactory glenoid trial is found, the surgeon removes the glenoid trial from the baseplate assembly and reads the position of the glenoid trial, which is measured relative to the adapter assembly. The surgeon then selects a glenoid implant that matches the size and shape of the glenoid trial that is selected during the trialing and replicates the position of the glenoid trial relative to the adapter assembly when constructing the glenoid implant. The glenoid implant is then installed on the baseplate assembly and is positioned in contact with the humeral cup to complete the assembly of the surgically created shoulder joint.

While known implants for reverse total shoulder arthroplasty and related implantation methods may have proven to be generally effective, a continuous need for improvement over the pertinent art remains.

SUMMARY

This section provides a general summary of the disclosure, and is not a comprehensive disclosure of its full scope or all of its features.

In accordance with one aspect, the subject disclosure provides a glenoid trial and implant assembly for use in reverse total shoulder arthroplasty. The glenoid trial and implant assembly generally includes a baseplate assembly, an adapter assembly, a glenoid trial, a glenoid implant, and a humeral cup. The baseplate assembly includes a glenoid baseplate component that has a primary bore. The glenoid baseplate component is configured to be fixed to a patient's glenoid during surgery. The adapter assembly includes an adapter and an adapter plate. The adapter has an adapter flange and a body portion that extends from the adapter flange to a medial body portion end. When the glenoid trial and implant assembly is assembled, the body portion of the adapter is received in the primary bore of the glenoid baseplate component. The glenoid trial is coupled to the adapter assembly when the glenoid trial and implant assembly is in a trialing configuration. The glenoid trial has a lateral glenoid trial face and a medial glenoid trial face. The lateral glenoid trial face has a bulbus shape and the medial glenoid trial face defines a glenoid trial cavity. The glenoid implant is coupled to the adapter assembly when the glenoid trial and implant assembly is in an installed configuration. The glenoid implant has a lateral glenoid implant face and a medial glenoid implant face. The lateral glenoid implant face has a bulbus shape and the medial glenoid implant face defines a glenoid implant cavity. The glenoid trial and the glenoid implant have the same size and shape or substantially the same size and shape such that the bulbus shape of the lateral glenoid implant face matches the bulbus shape of the lateral glenoid trial face.

The humeral cup is configured to be coupled to the patient's humerus during surgery and has a proximal surface. When the glenoid trial and implant assembly is in the trialing configuration, the proximal surface of the humeral cup abuts the lateral glenoid trial face. On the other hand, when the glenoid trial and implant assembly is in the installed configuration, the proximal surface of the humeral cup abuts the glenoid implant face. The adapter plate and the adapter of the adapter assembly are discrete components. When the adapter assembly is assembled however, the adapter plate is coupled to the adapter and the adapter plate abuts the adapter flange. When the glenoid trial and implant assembly is assembled in the trialing configuration, the adapter plate is received in the glenoid trial cavity. When the glenoid trial and implant assembly is assembled in the installed configuration, the adapter plate is received in the glenoid implant cavity. The glenoid trial and implant assembly includes a temporary connection that releasably couples the glenoid trial to the adapter assembly when the glenoid trial and implant assembly is assembled in the trialing configuration. Advantageously, the temporary connection provides separation of the glenoid trial from the adapter assembly without requiring disassembly of the adapter assembly. The glenoid trial and implant assembly also includes a permanent connection that fixedly couples the glenoid implant to the adapter assembly when the glenoid trial and implant assembly is assembled in the installed configuration. In some, but not all configurations of the subject glenoid trial and implant assembly, the temporary connection may be a magnetic connection between the glenoid trial and the adapter assembly.

In accordance with another aspect, the subject disclosure provides a humeral trial and implant assembly where the adapter assembly has an anti-rotation feature. The adapter includes a locking projection that extends from the medial body portion end. The baseplate assembly further includes a primary fastener that extends through the primary bore of the glenoid baseplate component and fixes the glenoid baseplate to the glenoid. The primary fastener includes a primary fastener head that has a rotation interface. The locking projection of the adapter is received in and engages the rotation interface of the primary fastener to prevent rotation of the adapter relative to the primary fastener, and thus the glenoid baseplate component, when the glenoid trial and implant assembly is in the trialing configuration and in the installed configuration.

In accordance with yet another aspect of the subject disclosure, a method of using the subject glenoid trial and implant assembly in total shoulder arthroplasty is provided. The method has a number of steps, including: installing the glenoid baseplate component in/on the glenoid, installing the humeral cup on the humerus, assembling the adapter assembly by installing the adapter plate on the adapter, inserting a body portion of the adapter into the primary bore in the glenoid baseplate component, placing the glenoid trial over the adapter plate of the adapter assembly, moving the humeral cup into contact with the glenoid trial, and moving the humerus through a range of motion. As the humerus is moved through the range of motion, the method includes observing whether the range of motion is undesirably restricted and whether there is undesirable play between the glenoid trial and the humeral cup. From the observations made during this step, the method includes determining whether the glenoid trial is of appropriate size. The method further includes the steps of: removing the glenoid trial from the adapter plate without disassembling the adapter assembly, separating the adapter assembly and the glenoid baseplate component by removing the body portion of the adapter from the primary bore of the glenoid baseplate component, installing the glenoid implant on the adapter plate of the adapter assembly, re-inserting the body portion of the adapter into the primary bore of the glenoid baseplate component, and moving the humeral cup into contact with the glenoid implant.

Several benefits are thus realized by the subject glenoid trial and implant assembly and the associated method. One benefit is reduced surgery time when compared to other glenoid trial and implant assemblies. Because the temporary connection between the glenoid trial and the adapter assembly allows the glenoid trial to be changed out without requiring disassembly of the adapter assembly, glenoid trials may be changed out more rapidly. Another benefit associated with the temporary connection between the glenoid trial and the adapter assembly is that a threaded fastener is not used to retain the glenoid trial on the adapter. Accordingly, the glenoid trial can be provided without the apical opening associated with the glenoid trials used in other glenoid trial and implant assemblies. Advantageously, the smooth and continuous surface of the glenoid trial provides a better approximation of the glenoid implant. Yet another benefit provided by the subject glenoid trial and implant assembly is that the adapter assembly may be used to couple both the glenoid trial and the glenoid implant to the glenoid baseplate component and can be interchanged for this purpose without disassembly. Because the temporary connection allows the adapter assembly to be removed from the glenoid trial without disassembly of the adapter assembly and because the locking projection prevents rotation of the adapter relative to the glenoid baseplate component, the positioning of the adapter relative to the glenoid baseplate component can be maintained and replicated each time the body portion of the adapter is re-inserted into the primary bore of the glenoid baseplate component. Therefore, the adapter assembly can simply be switched over to the glenoid implant and the surgeon does not need to read the position of the adapter plate during trialing and then attempt to replicate that position when constructing the glenoid implant. This also reduces surgery time and eliminates errors associated with the reading of the position of the adapter plate during trialing and the re-creation of the position in the glenoid implant. Another added benefit of the locking projection is that rotation of the body portion of the adapter within the primary bore of the glenoid baseplate component during trialing is prevented, which can provide undesirable false range of motion feedback. Advantageously, the locking projection eliminates this cause of false range of motion feedback.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 2 is a rear perspective view of an exemplary glenoid baseplate component of the exemplary glenoid trial and implant assembly shown in FIG. 1;

FIG. 3 is a cross-sectional view of the exemplary glenoid baseplate component taken along line 3-3 in FIG. 2;

FIG. 4 is a front perspective view of an exemplary primary fastener of the exemplary glenoid trial and implant assembly shown in FIG. 1;

FIG. 8 is an exploded rear perspective view of the exemplary adapter shown in FIG. 7;

FIG. 9 is a cross-sectional view of the exemplary adapter taken along line 9-9 in FIG. 7;

FIG. 10 is a partially exploded rear perspective view of the exemplary adapter assembly of FIG. 5 shown being installed on the glenoid baseplate component of FIG. 2;

FIG. 17 is a rear perspective view of an exemplary glenoid implant of the exemplary glenoid trial and implant assembly shown in FIG. 1;

FIG. 18 is a partially exploded rear perspective view of the exemplary adapter assembly of FIG. 5 and the exemplary glenoid implant of FIG. 17;

FIG. 19 is a rear perspective view of the exemplary adapter assembly of FIG. 5 shown installed in the exemplary glenoid implant of FIG. 17;

DETAILED DESCRIPTION

Figure 1:
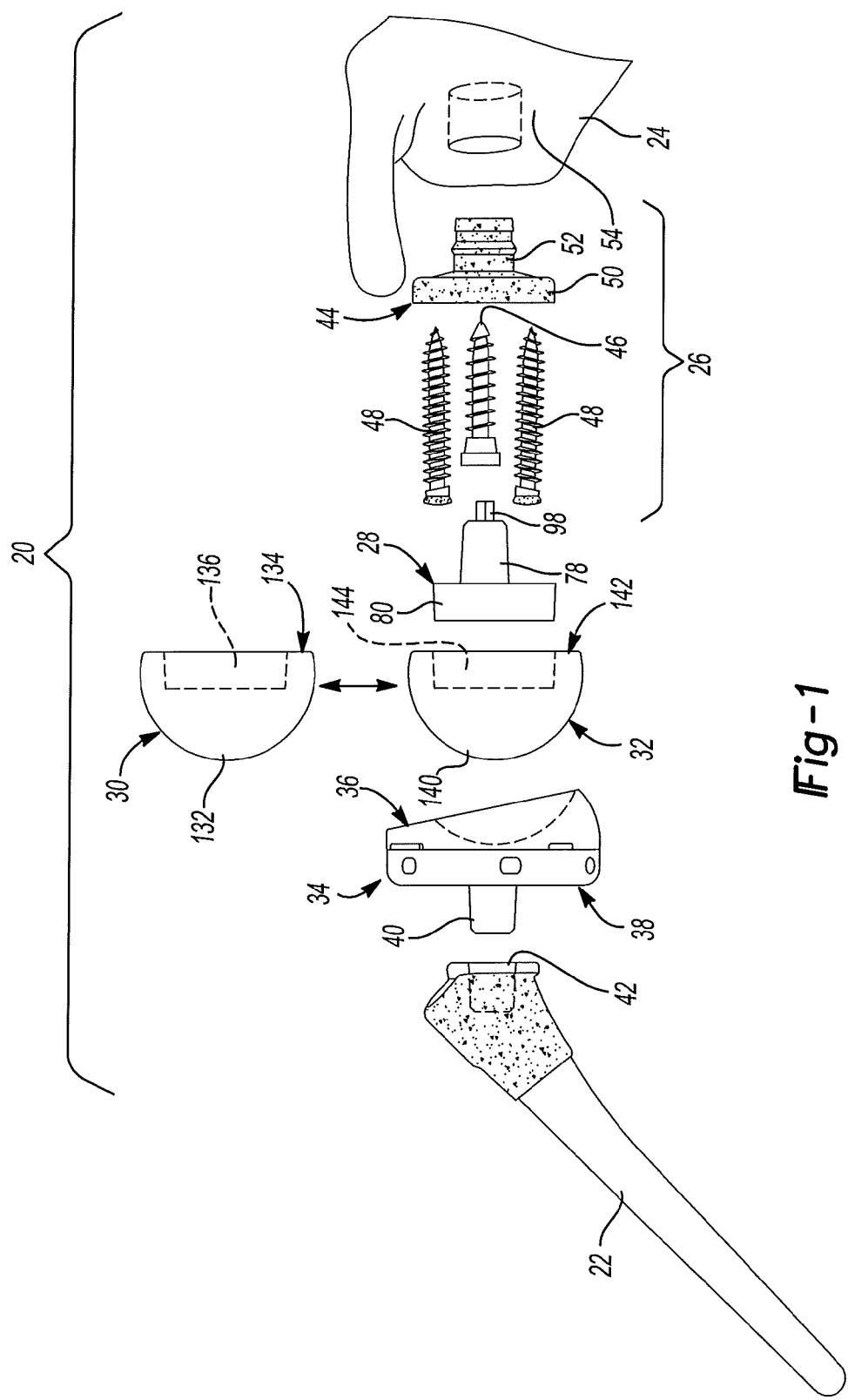
FIG. 1 is an exploded side elevation view of an exemplary glenoid trial and implant assembly constructed in accordance with the subject disclosure, where the exemplary glenoid trial and implant assembly is shown disposed between an exemplary humerus and glenoid.

Referring to the Figures, wherein like numerals indicate corresponding parts throughout the several views, a glenoid trial and implant assembly 20 for total shoulder arthroplasty is illustrated. It should be appreciated that the disclosed glenoid trial and implant assembly 20 generally falls into the categories of surgical implant assemblies and surgical implant kits. Therefore, the word "assembly" in "glenoid trial and implant assembly 20" may be replaced with the word "kit" without departing from the scope of the present disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as "abutting" or being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the Figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The glenoid trial and implant assembly 20 set forth herein may generally be used in shoulder joint replacement, shoulder resurfacing procedures, and other procedures related to the shoulder joint or the various bones of the shoulder joint, including the glenoid face or cavity of the scapula, the humeral head and adjacent shoulder bones. More particularly, the present teachings may be applied to reverse shoulder replacements, where the head or ball of the shoulder is disposed on the glenoid. This stands in contrast to anatomically correct shoulder replacements where the head or ball of the shoulder is disposed on the humerus. The glenoid trial and implant assembly 20 may include conventional implant components and/or patient-specific implant components and/or bone grafts that are prepared using computer-assisted image methods according to the present teachings. Computer modeling for obtaining three-dimensional images of the patient's anatomy using medical scans of the patient's anatomy (such as MRI, CT, ultrasound, X-rays, PET, etc.), the patient-specific prosthesis components and the patient-specific guides, templates and other instruments, can be prepared using various commercially available CAD programs and/or software available, for example, by Object Research Systems or ORS, Montreal, Canada.

The glenoid trial and implant assembly 20, when patient-specific, and any associated patient-specific implants and bone grafts can be generally designed and manufactured based on computer modeling of the patient's 3-D anatomic image generated from medical image scans including, for example, X-rays, MRI, CT, PET, ultrasound or other medical scans. Very small irregularities need not be incorporated in the three-dimensional engagement surface. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting guiding pins, K-wire, or other fasteners according to a surgeon-approved pre-operative plan.

The geometry, shape and orientation of the various elements of the glenoid trial and implant assembly 20, as well any patient-specific implants and bone grafts, if used, can be determined during the pre-operative planning stage of the procedure in connection with the computer-assisted modeling of the patient's anatomy. During the pre-operative planning stage, patient-specific instruments, custom, semi-custom or non-custom implants and other non-custom tools, can be selected and the patient-specific components can be manufactured for a specific-patient with input from a surgeon or other professional associated with the surgical procedure. Notwithstanding the foregoing, one of the benefits of the subject glenoid trial and implant assembly 20 is that such custom made implants and pre-operative planning is not required due to the use of trialing.

The glenoid trial and implant assembly 20 described herein may be used in reverse total shoulder arthoplasty. As shown in FIG. 1, the glenoid trial and implant assembly 20 is generally disposed between a humerus 22 and a glenoid 24 of a human body. The glenoid trial and implant assembly 20 includes a baseplate assembly 26, an adapter assembly 28, a glenoid trial 30, a glenoid implant 32, and a humeral cup 34. The glenoid 24 and the humerus 22 of the human body generally oppose one another and form part of an anatomical shoulder joint. As noted above, the glenoid trial and implant assembly 20 is used to surgically repair the anatomical shoulder joint. Thus, the baseplate assembly 26 is installed on the glenoid 24 and the humeral cup 34 is installed on the humerus 22 with the adapter assembly 28 and either the glenoid trial 30 or the glenoid implant 32 disposed between the baseplate assembly 26 and the humeral cup 34. It should be appreciated that the glenoid trial and implant assembly 20 may be assembled in two different configurations. These two different configurations include a trialing configuration and an installed configuration. In the trialing configuration, the shoulder joint that is surgically created by the glenoid trial and implant assembly 20 is tested using the glenoid trial 30. This glenoid trial 30 is a temporary component in the surgically created shoulder joint and may be selected from a plurality of glenoid trials 30 of varying shapes and sizes. It should be appreciated that the glenoid trial 30 may be classified as a "temporary component" in the sense that it is removed after trialing is completed and does not remain as part of the surgically created shoulder joint after completion of the surgery (i.e. post surgery). This stands in contrast to the baseplate assembly 26, for example, which is part of the surgically created shoulder joint during trialing and post surgery. In the installed configuration, the glenoid trial 30 is swapped out for the glenoid implant 32, which remains part of the surgically created shoulder joint after completion of the surgery (i.e. post surgery). Like the glenoid trial 30, the glenoid implant 32 may be selected from a plurality of glenoid implants 32 of varying shapes and sizes. Generally, the glenoid implant 32 that is chosen has the same shape and size as the glenoid trial 30 that is selected by trialing.

In the trialing configuration, the baseplate assembly 26 is disposed between the glenoid 24 and the glenoid trial 30 and the humeral cup 34 is disposed between the humerus 22 and the glenoid trial 30. Therefore, the glenoid trial 30 is disposed between the adapter assembly 28 the humeral cup 34 in the trialing configuration. In the installed configuration, the baseplate assembly 26 is disposed between the glenoid 24 and the glenoid implant 32 and the humeral cup 34 is disposed between the humerus 22 and the glenoid implant 32. Therefore, the glenoid implant 32 is disposed between the adapter assembly 28 the humeral cup 34 in the installed configuration. The humeral cup 34 presents a concave surface 36 and a back surface 38. The concave surface 36 of the humeral cup 34 abuts the glenoid trial 30 when the glenoid trial and implant assembly 20 is in the trialing configuration. Similarly, the concave surface 36 of the humeral cup 34 abuts the glenoid implant 32 when the glenoid trial and implant assembly 20 is in the installed configuration. The back surface 38 of the humeral cup 34 is coupled to the humerus 22 when the glenoid trial and implant assembly 20 is in the trialing configuration and when the glenoid trial and implant assembly 20 is in the installed configuration. For example and without limitation, the humeral cup 34 may include a protrusion 40 that extends outwardly from the back 38 of the humeral cup 34. The protrusion 40 may be received in a first surgical bore 42 created in the humerus 22. Obviously, alternative connections between the humeral cup 34 and the humerus 22 may be used and are considered within the scope of the subject disclosure.

With reference to FIGS. 1-4, the baseplate assembly 26 generally includes a glenoid baseplate component 44, a primary fastener 46, and one or more secondary fasteners 48. The subject disclosure includes a naming convention, where the term "medial" means that the associated element is oriented toward or faces the glenoid 24 and where the term "lateral" means that the associated element is oriented toward or faces the humerus 22. The glenoid baseplate component 44, which is shown by itself in FIGS. 2 and 3, includes a baseplate flange 50 and a boss 52 that extends from the baseplate flange 50. As shown in FIG. 1, the boss 52 is adapted to be received in a second surgical bore 54 created in the glenoid 24. The baseplate flange 50 may have a cylindrical shape and presents a lateral baseplate flange face 56 and a medial baseplate flange face 58. The boss 52 extends from the medial baseplate flange face 58 to a medial boss end 60. The glenoid baseplate component 44 also includes an interior baseplate surface 62. The interior baseplate surface 62 defines a primary bore 64 that extends from the lateral baseplate flange face 56 to the medial boss end 60. As such, the primary bore 64 extends through both the baseplate flange 50 and the boss 52. As best seen in FIG. 3, the interior baseplate surface 62 includes a tapered portion 66 extending to the lateral baseplate flange face 56 and a throat 68 of reduced diameter extending to the medial boss end 60. The boss 52 has a cylindrical shape and has an exterior boss surface 69. The exterior boss surface 69 includes a retention ring 70 that extends annularly about the boss 52 to prevent movement of the boss 52 within the second surgical bore 54 created in the glenoid 24.

The primary fastener 46 is received in the throat 68 of the primary bore 64 and extends from the medial boss end 60. The primary fastener 46 fixes the glenoid baseplate component 44 to the glenoid 24. As best seen in FIG. 4, the primary fastener 46 has a primary fastener head 72 presenting a rotation interface 74. The rotation interface 74 is configured to accept a tool for tightening the primary fastener 46. By way of example and without limitation, the rotation interface 74 may be configured to accept a hexagonal bit, which is sometimes referred to as a hex bit or Allen key. Obviously, the rotation interface 74 may be configured in alternative ways to accept other tools. Generally, the primary fastener 46 has been tightened (i.e. threaded into the glenoid 24) when the glenoid trial and implant assembly 20 is in the trialing configuration and when the glenoid trial and implant assembly 20 is in the installed configuration. As such, it is envisioned that the glenoid baseplate component 44 will be fixed to the glenoid 24 in both the trialing and installed configurations although circumstances may arise during surgery where it is not.

With reference to FIGS. 2 and 3, the baseplate flange 50 may optionally include one or more secondary bores 76 extending from the lateral baseplate flange face 56 to the medial baseplate flange face 58. A total of four secondary bores 76 are included in the configuration that is illustrated. Each of the secondary bores 76 are radially spaced from the primary bore 64 and may optionally be threaded. Notwithstanding, any number of secondary bores 76 may be provided without departing from the scope of the present disclosure. Each secondary bore 76 receives one of the secondary fasteners 48. Each secondary fastener 48 extends from the medial baseplate flange face 58 to fix the glenoid baseplate component 44 to the glenoid 24. Again, it is envisioned that the secondary fasteners 48 will be tightened when the glenoid trial and implant assembly 20 is in the trialing and installed configurations although circumstances may arise during surgery where they are not. It should also be appreciated that in alternative configurations, the glenoid baseplate component 44 may not include the boss 52 and may be fixed to the glenoid 24 in different ways that may or may not include the primary fastener 46 and/or the secondary fasteners 48. In another form, the primary fastener 46 may be integral with the glenoid baseplate component 44 such that the rotation interface 74 is formed in the glenoid baseplate component 44 itself.

Figure 5:
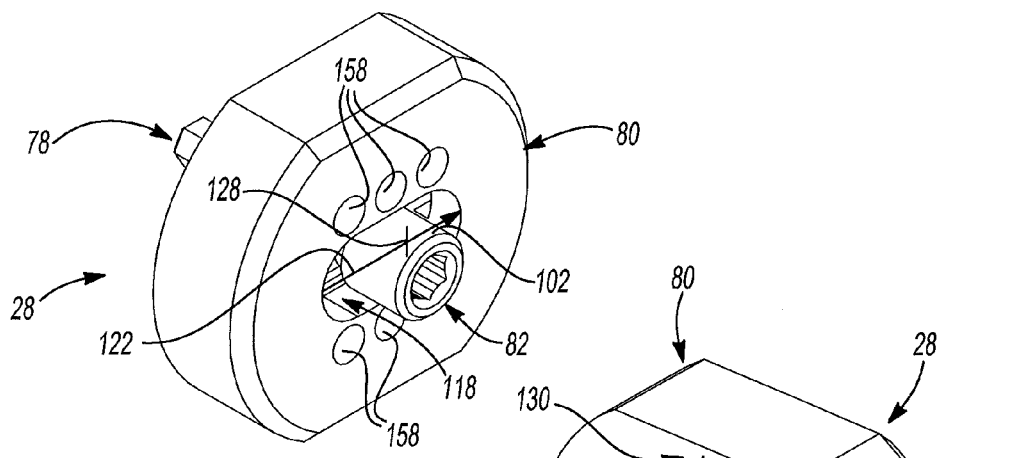
FIG. 5 is a front perspective view of an exemplary adapter assembly of the exemplary glenoid trial and implant assembly shown in FIG. 1.
Figure 6:
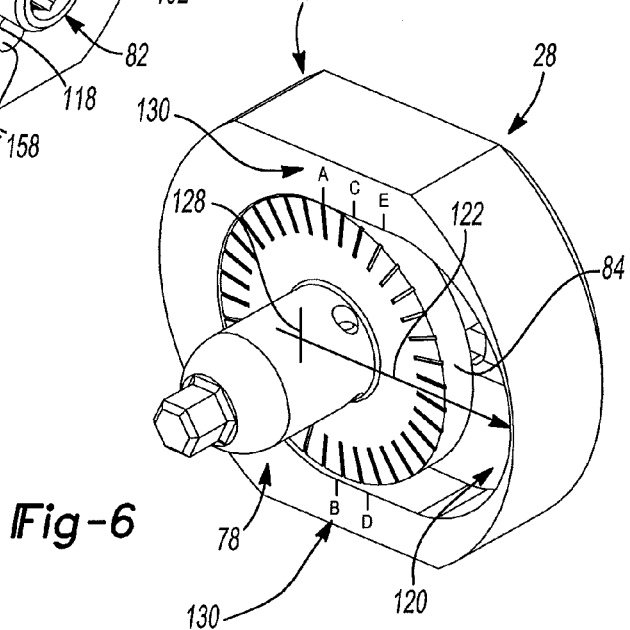
FIG. 6 is a rear perspective view of the exemplary adapter assembly shown in FIG. 5.
Figure 7:
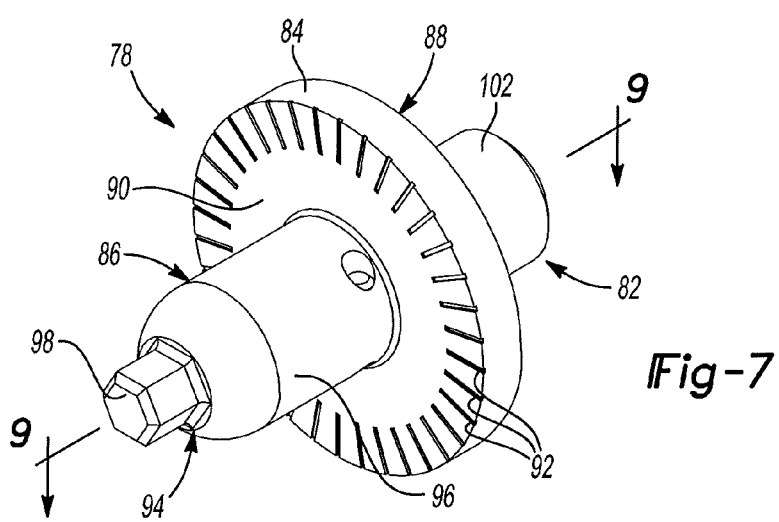
FIG. 7 is a rear perspective view of an exemplary adapter of the exemplary glenoid trial and implant assembly shown in FIG. 1.

As shown in FIGS. 5 and 6, the adapter assembly 28 of the glenoid trial and implant assembly 20 generally includes an adapter 78, an adapter plate 80, and an adapter fastener 82. With reference to FIGS. 7-9, the adapter 78 includes a adapter flange 84 and a body portion 86 that extends from the adapter flange 84. The adapter flange 84 presents a lateral adapter flange face 88 and a medial adapter flange face 90. The adapter flange 84 has a cylindrical shape and includes more than two demarcations 92 on the medial adapter flange face 90. The body portion 86 of the adapter flange 84 extends from the medial adapter flange face 90 to a medial body portion end 94. The body portion 86 of the adapter 78 may be generally cylindrical in shape and has a tapered outer surface 96. A locking projection 98 extends from the medial body portion end 94. The medial body portion end 94 has a shape that matches that of the rotation interface 74 of the primary fastener 46. The adapter 78 also includes an adapter bore 100, which may be threaded and that is open to the lateral adapter flange face 88. The adapter fastener 82 is received in the adapter bore 100 and includes an adapter fastener head 102 that projects from the lateral adapter flange face 88.

The adapter 78 further includes a pin bore 104 extending from the tapered outer surface 96 of the body portion 86 to the adapter bore 100. The pin bore 104 is transverse and tangent to the adapter bore 100. The adapter fastener 82 includes a first stop 106 that is spaced from the adapter fastener head 102 and a second stop 108 that is spaced from the first stop 106. The first and second stops 106, 108, which may be threaded, extend annularly about the adapter fastener 82 to create an annular space 110 that is axially between the first and second stops 106, 108 and radially between the adapter fastener 82 and the body portion 86 of the adapter 78. The pin bore 104 is positioned along the body portion 86 of the adapter 78 such that the pin bore 104 is open to the annular space 110 between the first and second stops 106, 108 of the adapter fastener 82. The adapter assembly 28 further includes a pin 112 that is received in the pin bore 104. When installed, the pin 112 limits axial movement of the adapter fastener 82 within the adapter bore 100 by contacting the first and second stops 106, 108 of the adapter fastener 82, which form opposing travel limits. In this way, the adapter 78 and the adapter fastener 82 may be preassembled where the adapter fastener 82 is not tightened and can freely rotate within the adapter bore 100 while being retaining therein by the pin 112.

Figure 11:
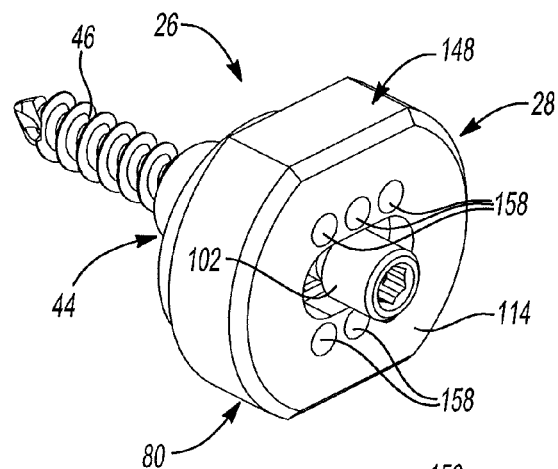
FIG. 11 is a front perspective view of the exemplary adapter assembly of FIG. 5 shown installed on the glenoid baseplate component of FIG. 2.

As illustrated in FIGS. 10 and 11, the body portion 86 of the adapter 78 is received in the primary bore 64 of the glenoid baseplate component 44. As will be explained further in the method set forth below, it is envisioned that the body portion 86 of the adapter 78 will be disposed in the primary bore 64 of the glenoid baseplate component 44 when the glenoid trial and implant assembly 20 is in the trialing configuration and when the glenoid trial and implant assembly 20 is in the installed configuration. Generally, the body portion 86 of the adapter 78 may be loosely inserted into the primary bore 64 of the glenoid baseplate component 44 when the glenoid trial and implant assembly 20 is in the trialing configuration so that the adapter assembly 28 can be easily removed or separated from the glenoid baseplate component 44 for changing out glenoid trials 30 or installing the glenoid implant 32. The body portion 86 of the adapter 78 may then be firmly pressed into the primary bore 64 of the glenoid baseplate component 44 when the glenoid trial and implant assembly 20 is in the installed configuration so that the adapter assembly 28 will not separate from the glenoid baseplate component 44. To this end, when the body portion 86 of the adapter 78 is pressed into the primary bore 64 of the glenoid baseplate component 44, the tapered outer surface 96 of the body portion 86 mates with the tapered portion 66 of the interior baseplate surface 62. This helps to prevent separation of the adapter 78 and the glenoid baseplate component 44 when the glenoid trial and implant assembly 20 is in the installed configuration.

As noted above, the locking projection 98 of the adapter 78 extends from the medial body portion end 94 and has a shape that matches that of the rotation interface 74 of the primary fastener 46. When the body portion 86 of the adapter 78 is inserted into the primary bore 64 of the glenoid baseplate component 44, the locking projection 98 is received in and engages the rotation interface 74 of the primary fastener 46 to prevent rotation of the adapter 78 relative to the primary fastener 46 and the glenoid baseplate component 44. Therefore, the locking projection 98 cooperates with the rotation interface 74 of the primary fastener 46 to rotationally fix the adapter 78 in place when the glenoid trial and implant assembly 20 is in the trialing configuration and when the glenoid trial and implant assembly 20 is in the installed configuration. Although other shapes may be used without departing from the scope of the present disclosure, both the locking projection 98 of the adapter 78 and the rotation interface 74 of the primary fastener 46 shown in the figures have hexagonal shapes. Another added benefit of the locking projection 98 is that it prevents rotation of the adapter 78 within the primary bore 64 of the glenoid baseplate component 44 during trialing. This is advantageous because such rotation can create false range of motion feedback during trialing.

Figure 12:
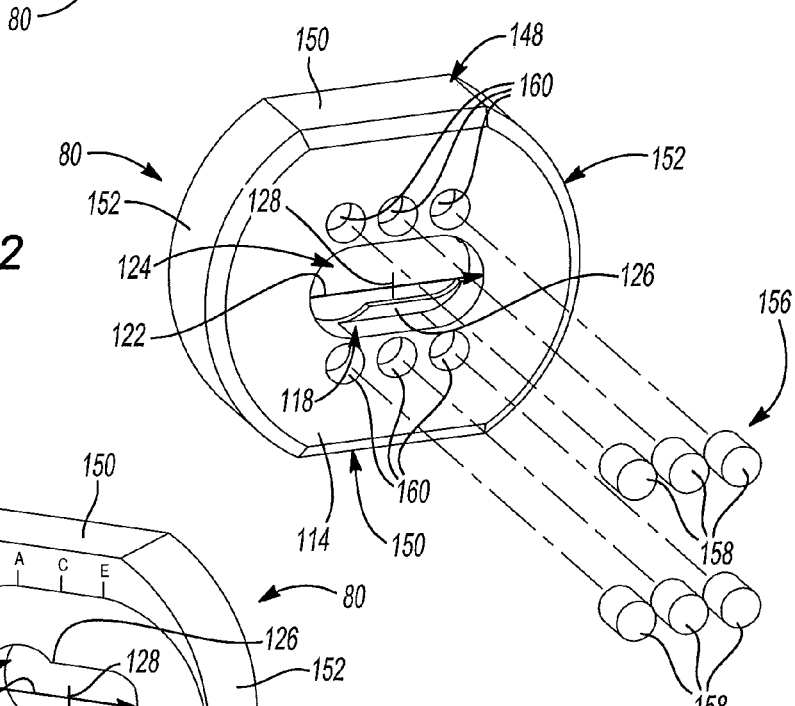
FIG. 12 is an exploded front perspective view of an exemplary adapter plate of the exemplary glenoid trial and implant assembly shown in FIG. 1.
Figure 13:
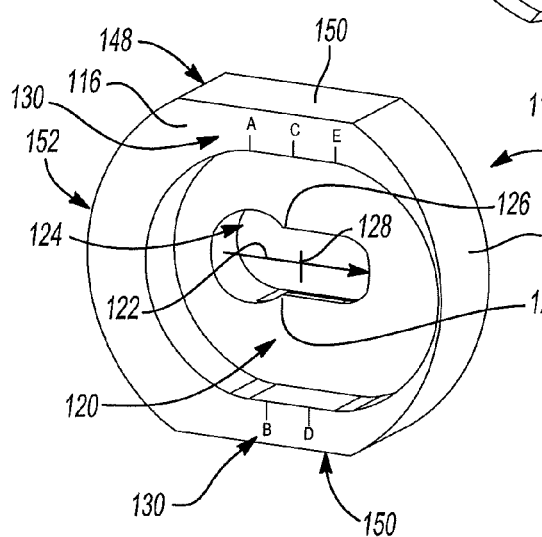
FIG. 13 is a rear perspective view of the exemplary adapter plate shown in FIG. 12.

As shown throughout the views, the adapter plate 80 and the adapter 78 of the adapter assembly 28 are separate, discrete components. When the adapter assembly 28 is assembled as shown in FIGS. 5 and 6, the adapter plate 80 abuts the adapter flange 84 and the adapter fastener 82 couples the adapter plate 80 to the adapter 78. With reference to FIGS. 12 and 13, the adapter plate 80 is shown by itself. The adapter plate 80 has a lateral adapter plate face 114 and a medial adapter plate face 116. The lateral adapter plate face 114 defines a lateral anterior adapter plate cavity 118 that has a slot-like shape. The medial adapter plate face 116 defines a medial adapter plate cavity 120 that receives the adapter flange 84 when the adapter assembly 28 is assembled (see FIG. 6). The medial adapter plate cavity 120 is larger than the adapter flange 84 and is elongated along an offset direction 122 such that the adapter 78 may be shifted relative to the adapter plate 80 in the offset direction 122 when the glenoid trial and implant assembly 20 is in the trialing configuration. It should be appreciated that the locking projection 98 works in tandem with the structure of the adapter flange 84 and the medial adapter plate cavity 120 to provide this range of adjustment because the locking projection 98 acts to prevent movement of the adapter 78 when the adapter plate 80 is being shifted and rotated into position. Advantageously, the range of adjustment this feature provides gives surgeons greater flexibility in locating the glenoid trial 30 and later the glenoid implant 32. Such flexibility in the positioning of the glenoid trial 30 and later the glenoid implant 32 can be particularly beneficial where anatomical structures, abnormalities, or damage to the shoulder joint limits the placement of the glenoid baseplate component 44 and/or would otherwise interfere with the range of motion of the humerus 22.

The adapter plate 80 includes a pass-through 124 that extends between and that is open to the lateral adapter plate cavity 118 and the medial adapter plate cavity 120. The pass-through 124 may have a key-hole shape. The key-hole shape of the pass-through 124 is created by ribs 126 that that extend into the pass-through 124 and that are disposed between the lateral adapter plate cavity 118 and the medial adapter plate cavity 120. The adapter fastener 82 extends through the pass-through 124 and into the adapter bore 100 to selectively fix the adapter plate 80 to the adapter 78. The pass-through 124 is also elongated along the offset direction 122 such that the adapter 78 may be shifted relative to the adapter plate 80 in the offset direction 122 when the glenoid trial and implant assembly 20 is in the trialing configuration. With reference to both FIGS. 5-6 and 12-13, the adapter fastener head 102 can be tightened against the ribs 126 in the pass-through 124 to fix the adapter plate 80 in place relative to the adapter 78 at an offset position 128 located along the offset direction 122. In this way, the offset position 128 of the adapter plate 80 relative to the adapter 78 can be adjusted in the trialing configuration and is then set by tightening the adapter fastener 82. This locks the adapter plate 80 in the offset position 128 that is designated during trialing such that the offset position 128 is maintained when the glenoid trial and implant assembly 20 is in the installed configuration.

As best seen in FIGS. 6 and 13, the medial adapter plate face 116 includes a plurality of labeled demarcations 130 adjacent the medial adapter plate cavity 120 that provide an offset position measurement. The offset position measurement may be determined by identifying which one of the labeled demarcations 130 on the medial adapter plate face 116 is aligned with one of the demarcations 92 on the medial adapter flange face 90. The offset position measurement may then be used by the surgeon to set the offset position 128 of the adapter assembly 28 in the installed configuration, where the same adapter assembly 28 is not used in both the trialing configuration and the installed configuration. However, one notable advantage of the adapter assembly 28 described herein over other implant assemblies, is that the disclosed adapter assembly 28 may optionally be used in both the trialing and installed configurations. Therefore, the offset position measurement from the glenoid trial 30 need not be replicated for the glenoid implant 32 because the adapter assembly 28 from the trialing configuration can simply be reused in the installed configuration. This reduces surgery time and minimizes error because the surgeon does not need to read the offset measurement position and replicate it in the glenoid implant 32.

Figure 14:
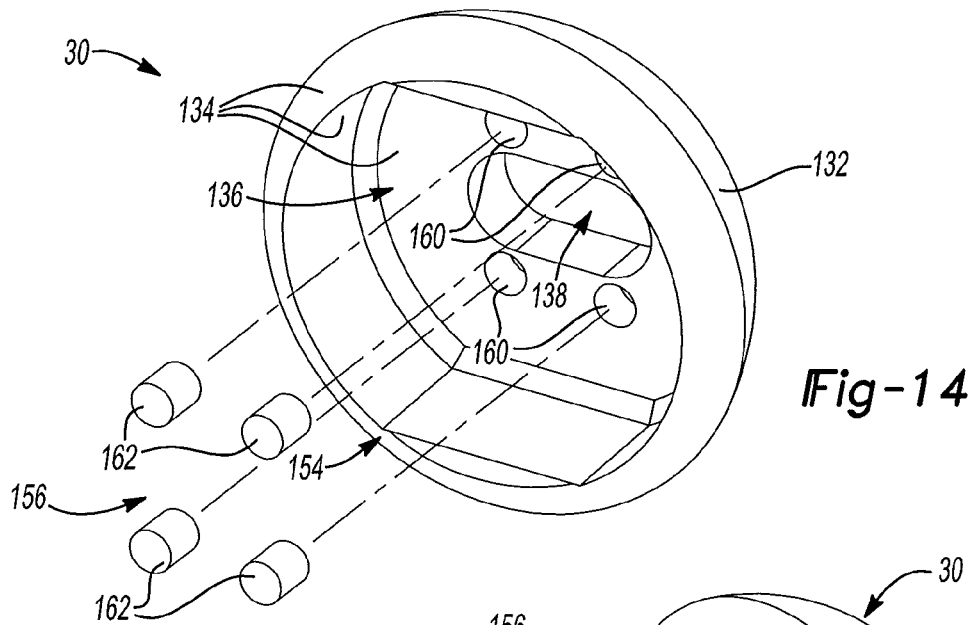
FIG. 14 is an exploded rear perspective view of an exemplary glenoid trial of the exemplary glenoid trial and implant assembly shown in FIG. 1.
Figure 15:
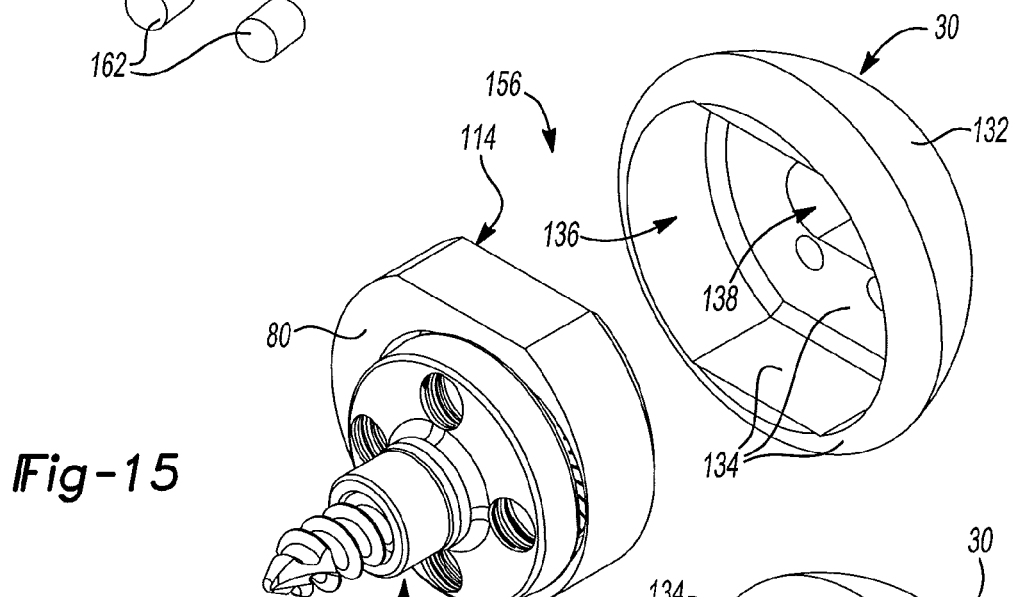
FIG. 15 is a partially exploded rear perspective view of the exemplary glenoid trial of FIG. 14 being installed on the exemplary adapter assembly of FIG. 5 and the exemplary glenoid baseplate component of FIG. 2.
Figure 16:
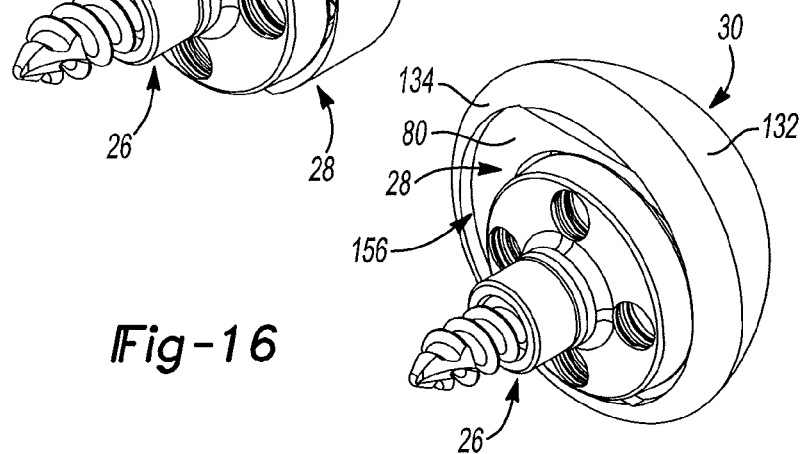
FIG. 16 is a rear perspective view of the exemplary glenoid trial of FIG. 14 shown installed on the exemplary adapter assembly of FIG. 5 and the exemplary glenoid baseplate component of FIG. 2.

With reference to FIGS. 14-16, the glenoid trial 30 is shown. The glenoid trial 30 has a lateral glenoid trial face 132 that has a bulbus shape and a medial glenoid trial face 134 that defines a glenoid trial cavity 136. It should be appreciated that the lateral glenoid trial face 132 abuts the concave surface 36 of the humeral cup 34 when the glenoid trial and implant assembly 20 is in the trialing configuration. To provide clearance for the adapter fastener head 102, the glenoid trial cavity 136 may additionally include a first fastener head pocket 138. It should be appreciated that the first fastener head pocket 138 does not extend through the glenoid trial 30 to the lateral glenoid trial face 132. As shown in FIGS. 15 and 16, the glenoid trial 30 is temporarily coupled to the adapter assembly 28 when the glenoid trial and implant assembly 20 is in the trialing configuration. Specifically, the adapter plate 80 of the adapter assembly 28 is received in the glenoid trial cavity 136 when the glenoid trial and implant assembly 20 is in the trialing configuration. Accordingly, the lateral adapter plate face 114 is disposed within the glenoid trial cavity 136 adjacent the medial glenoid trial face 134 when the glenoid trial and implant assembly 20 is in the trialing configuration. Again, the glenoid trial 30 may be selected from a plurality of glenoid trials 30 of varying shapes and sizes. For example and without limitation, the bulbus shape of the lateral glenoid trial face 132 of the different glenoid trials 30 may be hemispherical or oblong and may have different dimensions. As will be explained in greater detail below, the glenoid trial 30 and the adapter plate 80 are configured such that the glenoid trial 30 can be separated from the adapter plate 80 of the adapter assembly 28 in a quick and easy manner. This allows surgeons to rapidly change out different glenoid trials 30 until a satisfactory fit is found.

Figure 20:
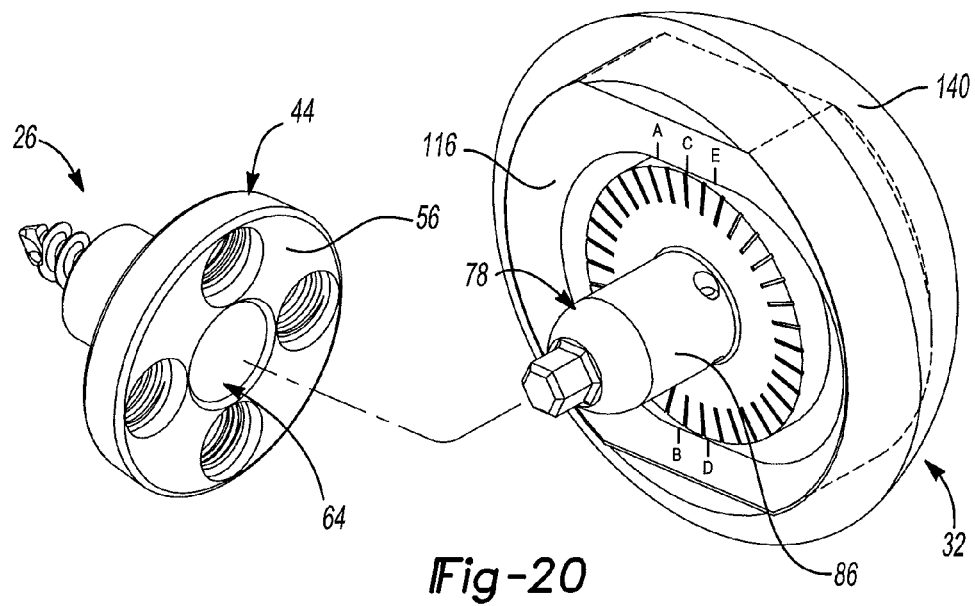
FIG. 20 is a partially exploded rear perspective view of the exemplary glenoid implant of FIG. 17 shown installed on the exemplary adapter assembly of FIG. 5 where the adapter assembly is being installed on the exemplary glenoid baseplate component of FIG. 2.
Figure 21:
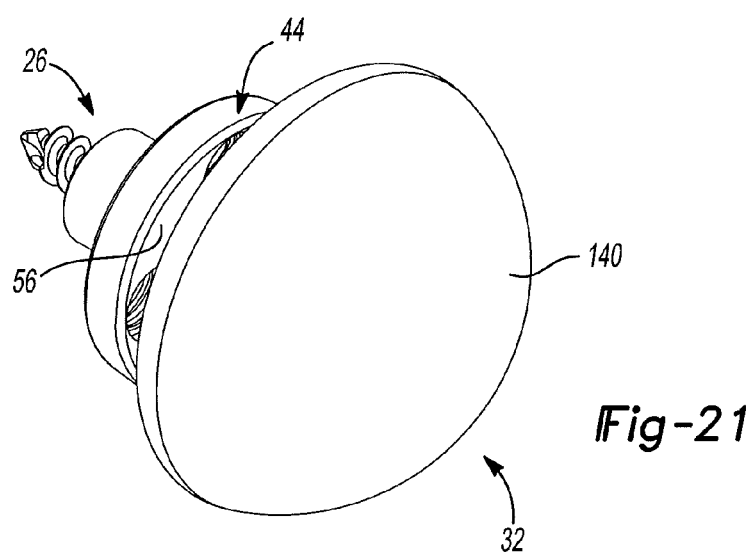
FIG. 21 is a front perspective view of the exemplary glenoid implant of FIG. 17 shown installed on the exemplary adapter assembly of FIG. 5 and the exemplary glenoid baseplate component of FIG. 2.

With reference to FIGS. 17-21, the glenoid implant 32 is shown. The glenoid implant 32 has a lateral glenoid implant face 140 that has a bulbus shape and a medial glenoid implant face 142 that defines a glenoid implant cavity 144. It should be appreciated that the lateral glenoid implant face 140 abuts the concave surface 36 of the humeral cup 34 when the glenoid trial and implant assembly 20 is in the installed configuration. To provide clearance for the adapter fastener head 102, the glenoid implant cavity 144 may additionally include a second fastener head pocket 146. It should be appreciated that the second fastener head pocket 146 does not extend through the glenoid implant 32 to the lateral glenoid implant face 140. Again, the glenoid implant 32 may be selected from a plurality of glenoid implants 32 of varying shapes and sizes. Generally, the glenoid implant 32 is selected to have the same shape and size (i.e. dimensions) as the glenoid trial 30 that is selected by the surgeon during trialing. Therefore, the bulbus shape of the lateral glenoid implant face 140 will match the bulbus shape of the lateral glenoid trial face 132. Unlike the glenoid trial 30, the glenoid implant 32 is permanently coupled to the adapter assembly 28. As shown in FIGS. 18 and 19, the adapter plate 80 of the adapter assembly 28 is received in the glenoid implant cavity 144 when the glenoid trial and implant assembly 20 is in the installed configuration. Accordingly, the lateral adapter plate face 114 is disposed in the glenoid implant cavity 144 adjacent the medial glenoid implant face 142 when the glenoid trial and implant assembly 20 is in the installed configuration. As shown in FIGS. 20 and 21, the glenoid implant 32 and adapter assembly 28 are then installed on the glenoid baseplate component 44 by pressing the body portion 86 of the adapter 78 into the primary bore 64 of the glenoid baseplate component 44.

When the glenoid trial and implant assembly 20 is in the trialing configuration and when the glenoid trial and implant assembly 20 is in the installed configuration, the medial adapter plate face 116 abuts the lateral baseplate flange face 56 (see FIGS. 16 and 21). Additionally, the adapter fastener head 102 is entirely covered by the glenoid trial 30 in the trialing configuration and is entirely covered by the glenoid implant 32 in the installed configuration. As best seen in FIGS. 12 and 13, the adapter plate 80 includes a periphery 148 having a non-circular shape. Although the non-circular shape of the periphery 148 may take a variety of different forms, the periphery 148 of the adapter plate 80 illustrated includes a pair of opposing flat faces 150 that are spaced by a pair of opposing curved faces 152. As best seen in FIGS. 14 and 17, the glenoid trial cavity 136 and the glenoid implant cavity 144 both have a geometry 154 that corresponds to the non-circular shape of the periphery 148. This geometric relationship prevents the glenoid trial 30 from rotating with respect to the adapter plate 80 when the adapter plate 80 is received within the glenoid trial cavity 136. Similarly, the glenoid implant 32 cannot rotate with respect to the adapter plate 80 when the adapter plate 80 is received within the glenoid implant cavity 144 in the installed configuration. When combined with the locking projection 98, the glenoid implant 32 is rotationally fixed with respect to the glenoid baseplate component 44 and thus the glenoid 24 in the installed configuration. However, in some configurations, the glenoid trial 30 may be rotated with respect to the glenoid 24 baseplate during trialing to position the glenoid trial 30. If the adapter fastener 82 is not tightened in the trialing configuration, then the glenoid trial 30 and adapter plate 80 are free to rotate with respect to the adapter 78 even though the locking projection 98 prevents the adapter 78 from rotating with respect to the glenoid baseplate component 44.

With reference to FIGS. 14-16, a temporary connection 156 releasably couples the glenoid trial 30 to the adapter assembly 28. The temporary connection 156 allows for rapid separation of the glenoid trial 30 from the adapter assembly 28 without requiring disassembly of the adapter assembly 28. Because separation can occur without disassembly of the adapter assembly 28, the temporary connection 156 allows for the rapid separation of the glenoid trial 30 and adapter assembly 28 while maintaining or preserving the offset position 128 of the adapter plate 80 relative to the adapter 78. The offset position 128 is preserved because the glenoid trial 30 can be removed without loosening the adapter fastener 82. As the term is used herein, "temporary connection" encompasses any connection between the glenoid trial 30 and the adapter assembly 28 that can be released, severed, separated, disconnected, or decoupled without requiring disassembly of the adapter assembly 28. For example and without limitation, such a temporary connection 156 could include a magnetic connection between the glenoid trial 30 and the adapter assembly 28, threads disposed on the glenoid trial cavity 136 and the periphery 148 of the adapter plate 80, a removable clip interconnecting the glenoid trial 30 and the adapter assembly 28, or a tongue and groove connection between the glenoid trial 30 and the adapter assembly 28. The temporary connection 156 is not a threaded fastener coupling the glenoid trial 30 to the adapter assembly 28. Advantageously, the temporary connection 156 between the glenoid trial 30 and the adapter assembly 28 dramatically reduces trialing time by simplifying and shortening the process for changing out glenoid trials 30. Unlike in other implant assemblies, the glenoid trial 30 may be changed out without disassembling the adapter assembly 28. This also means that the offset position 128 of the adapter plate 80 relative to the adapter 78 can be maintained when changing out glenoid trials 30 and does not have to be reset each time a glenoid trial 30 is changed out. Another added benefit is that the temporary connection 156 allows the lateral glenoid trial face 132 to be completely smooth just like the lateral glenoid implant face 140. Because there is no threaded fastener attaching the glenoid trial 30 to the adapter assembly 28, the lateral glenoid trial 30 does not require an apical opening for receiving such a threaded fastener. Elimination of the apical opening from the glenoid trial 30 is advantageous because it has been found that the apical opening on other glenoid trials can catch on anatomical features of the shoulder joint or hardware during trialing and provide false range of motion feedback.

With reference to FIG. 12 and FIGS. 14-16, the temporary connection 156 shown is a magnetic connection between the glenoid trial 30 and the adapter assembly 28. In accordance with this configuration, the adapter plate 80 includes one or more adapter plate magnets 158 that releasably hold the glenoid trial 30 on the adapter plate 80. As illustrated, the adapter plate 80 includes one or more magnet cavities 160 that are open to the lateral adapter plate face 114. These magnet cavities 160 in the adapter plate 80 each receive one of the adapter plate magnets 158 such that the adapter plate magnets 158 are embedded in the adapter plate 80. The glenoid trial 30 may additionally or alternatively include one or more glenoid trial magnets 162 that releasably hold the glenoid trial 30 on the adapter plate 80. As such, the glenoid trial 30 may include one or more magnet cavities 160 that are open to the medial glenoid trial face 134. These magnet cavities 160 in the glenoid trial 30 each receive one of the glenoid trial magnets 162 such that the glenoid trial magnets 162 are embedded in the glenoid trial 30. Therefore, several combinations exist where the magnetic connection may include only the adapter plate magnets 158 in the adapter plate 80, only the glenoid trial magnets 162 in the glenoid trial 30, or both the adapter plate magnets 158 in the adapter plate 80 and the glenoid trial magnets 162 in the glenoid trial 30. Obviously, the number and placement of the magnets may vary from those shown in the figures without departing from the scope of the subject disclosure.

In contrast to the temporary connection 156 between the glenoid trial 30 and the adapter assembly 28, a permanent connection 164 fixedly couples the glenoid implant 32 to the adapter assembly 28. As the term is used herein, "permanent connection" encompasses any connection between the glenoid implant 32 and the adapter assembly 28 that is designed or intended to remain in place post-surgery. For example and without limitation, such a permanent connection 164 could include a press fit between the glenoid implant 32 and the adapter assembly 28 or an adhesive, glue, epoxy, binder, or cement connection between the glenoid implant 32 and the adapter assembly 28. Therefore, it is conceivable that such a "permanent connection" could be separated by prying the glenoid implant 32 from the adapter assembly 28 with a tool or other instrument or by breaking the glenoid implant 32 and/or adapter assembly 28. In FIGS. 17-19, the permanent connection 164 shown is a press fit between the periphery 148 of the adapter plate 80 and the medial glenoid implant face 142 at the glenoid implant cavity 144. Specifically, the periphery 148 of the adapter plate 80 and the medial glenoid implant face 142 at the glenoid implant cavity 144 may each include complementary tapers 166 such that the adapter plate 80 becomes fixed to the glenoid implant 32 when the adapter assembly 28 is pressed into the glenoid implant cavity 144. Such complementary tapers 166 could be, without limitation, Morse tapers, which are well known permanent connections in the field of surgical implant assemblies.

Figure 22:
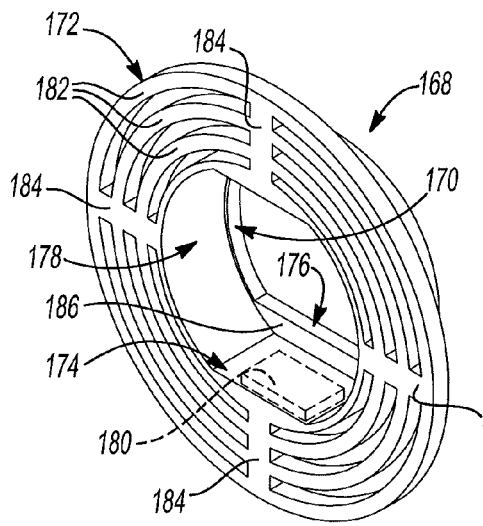
FIG. 22 is a rear perspective view of an exemplary positioning guide of the exemplary glenoid trial and implant assembly.
Figure 23:
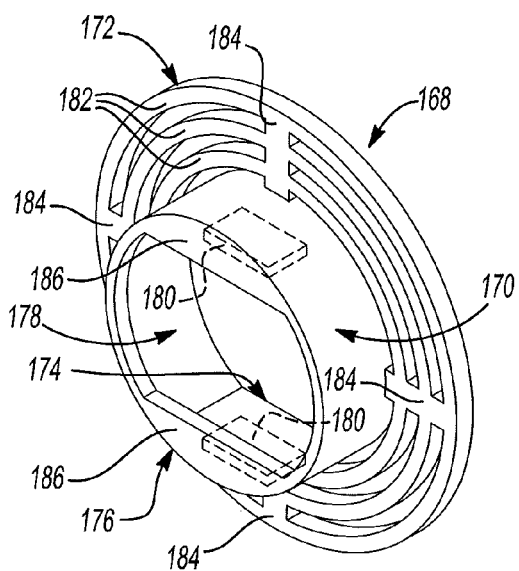
FIG. 23 is a front perspective view of the exemplary positioning guide shown in FIG. 22.
Figure 24:
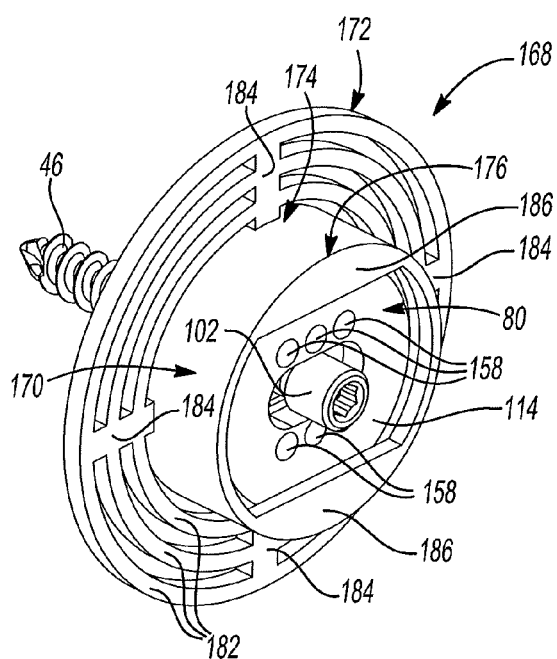
FIG. 24 is a front perspective view of the exemplary positioning guide of FIG. 22 shown installed on the exemplary adapter assembly of FIG. 5 and the glenoid baseplate component of FIG. 2.

Referring now to FIGS. 22-24, the glenoid trial and implant assembly 20 may optionally include a positioning guide 168. The positioning guide 168 generally includes a hub 170 and a positioning guide flange 172 that extends outwardly from the hub 170. The hub 170 extends between a medial hub end 174 and an lateral hub end 176. The hub 170 has a hub cavity 178 that receives the adapter plate 80. As shown in FIG. 24, the hub cavity 178 mates with the periphery 148 of the adapter plate 80 when the glenoid trial and implant assembly 20 is in the trialing configuration. Optionally, the positioning guide 168 may be magnetically retained on the adapter plate 80. In accordance with this configuration, the positioning guide 168 may include one or more positioning guide magnets 180 embedded in the hub 170 that releasably hold the positioning guide 168 on the adapter plate 80. Alternatively, the positioning guide 168 may be ferromagnetic such that the adapter plate magnets 158 hold the positioning guide 168 on the adapter plate 80.

The positioning guide flange 172 extends outwardly from the medial hub end 174 and includes a plurality of annular rings 182 each representing different glenoid trial/implant sizes. The plurality of annular rings 182 are interconnected to one another and to the hub 170 by a plurality of spokes 184 that extend radially from the medial hub end 174. Of course the positioning guide flange 172 may be constructed in other ways. By way of example and without limitation, the positioning guide flange 172 may be a solid disc and the plurality of annular rings 182 may be raised projections or other demarcations that are provided on the positioning guide flange 172. The positioning guide 168 may also include wall 186 extending inwardly from the lateral hub end 176 that abuts the lateral adapter plate face 114 when the positioning guide 168 is placed on the adapter assembly 28. Accordingly, the medial adapter plate face 114 prevents over insertion of the adapter plate 80 in the hub cavity 178 of the positioning guide 168. From FIG. 24, it should be appreciated that the positioning guide 168 may be placed on the adapter plate 80 of the adapter assembly 28 after the glenoid baseplate component 44 has been installed on the glenoid 24 and after the adapter assembly 28 has been assembled. With the positioning guide 168 fitted on the adapter plate 80, the surgeon inserts the body portion 86 of the adapter 78 into the primary bore 64 of the glenoid baseplate component 44. Then the surgeon uses the positioning guide 168 to determine the offset position 128 of the adapter plate 80 relative to the adapter 78 and a starting glenoid trial/implant size. This process is done while shifting and rotating the positioning guide 168 relative to the glenoid 24, which is accompanied by an associated shifting and rotation of the adapter plate 80 relative to the adapter 78. Once a satisfactory offset position 128 is found, the surgeon then tightens the adapter fastener 82 thereby locking the offset position 128 of the adapter plate 80 in place relative to the adapter 78. The positioning guide 168 is then removed and the glenoid trial 30 corresponding to the starting glenoid trial/implant size is placed on the adapter assembly 28 for trialing.

It should be appreciated that the various components of the glenoid trial and implant assembly 20 may be made of a wide variety of different materials. Often material selection is limited by health regulations that specify those materials which may be surgically implanted into the human body. Such heath regulations are often country specific and are often in a state of flux. In the exemplary configuration shown throughout the figures, the various components of the baseplate assembly 26, the various components of the adapter assembly 28, the glenoid trial 30, the glenoid implant 32, and the humeral cup 34 may be made from medical grade titanium, cobalt chrome, plastic, or a combination of these materials. The positioning guide 168 may also be made from a variety of different materials, including plastic for example. Notwithstanding, it should be appreciated that these recitations of possible materials are merely exemplary and are not intended as limiting.

A method of using the glenoid trial and implant assembly 20 set forth above in total shoulder arthroplasty is also provided. The method includes a plurality of steps, which are described below. The method includes surgically implanting a glenoid baseplate component 44 into a glenoid 24, inserting a primary fastener 46 into a primary bore 64 created in the glenoid baseplate component 44, and fixing the glenoid baseplate component 44 to the glenoid 24 by tightening the primary fastener 46. In accordance with the above steps, the disclosed baseplate assembly 26 may be installed. The method also includes surgically coupling a humeral cup 34 to a humerus 22 and assembling an adapter assembly 28 by installing an adapter plate 80 on an adapter 78. The step of assembling the adapter 78 may further include inserting an adapter flange 84 of the adapter 78 into a medial adapter plate cavity 120 of the adapter plate 80 and inserting an adapter fastener 82 through a pass-through 124 in the adapter plate 80 and into an adapter bore 100 of the adapter 78 to couple the adapter plate 80 to the adapter 78. In accordance with the above steps, the disclosed adapter assembly 28 may be assembled.

In accordance with the method, the step of inserting a body portion 86 of the adapter 78 into the primary bore 64 of the glenoid baseplate component 44 may be performed. The step of inserting the body portion 86 of the adapter 78 into the primary bore 64 may further include inserting a locking projection 98 extending from the body portion 86 of the adapter 78 into a rotation interface 74 of the primary fastener 46 to lock rotation of the adapter 78 relative to the primary fastener 46 and the glenoid baseplate component 44. As discussed in the above description of the glenoid trial and implant assembly 20, the method may optionally include the steps of placing a positioning guide 168 over the adapter plate 80 where the positioning guide 168 has a plurality of annular rings 182 that each represent different glenoid trial sizes and retaining the positioning guide 168 on the adapter plate 80 by magnetism. The method further includes positioning the adapter plate 80 relative to the glenoid baseplate component 44 by rotating and sliding the adapter plate 80 relative to the glenoid baseplate component 44 and the adapter 78 and tightening the adapter fastener 82 to lock the adapter plate 80 in place at a pre-determined offset position 128 relative to the glenoid baseplate component 44 and the adapter 78. Where the positioning guide 168 is used, the method may include the steps of using the plurality of annular rings 182 on the positioning guide 168 to help locate the pre-determined offset position 128 and then removing the positioning guide 168 from the adapter plate 80.

In accordance with the trialing procedure introduced above, the method includes the steps of placing a glenoid trial 30 over the adapter plate 80 of the adapter assembly 28, retaining the glenoid trial 30 on the adapter plate 80 by magnetism, moving the humeral cup 34 into contact with the glenoid trial 30, and moving the humerus 22 through a range of motion and observing the fit and function of the glenoid trial 30 (i.e. whether the range of motion is undesirably restricted and whether there is undesirable play between the glenoid trial 30 and the humeral cup 34). The step of determining whether the pre-determined offset position 128 of the adapter plate 80 is appropriate and whether the glenoid trial 30 is of appropriate size is performed based upon the observations made during the step of moving the humerus 22 through the range of motion. In accordance with this trialing procedure, the method includes removing the glenoid trial 30 from the adapter plate 80 without disassembling the adapter assembly 28 and may further include repeating the steps of positioning the adapter plate 80, tightening the adapter fastener 82, placing the glenoid trial 30 over the adapter plate 80, moving the humeral cup 34 into contact with the glenoid trial 30, and moving the humerus 22 through a range of motion at different offset positions 128 of the adapter plate 80 in response to determining that the pre-determined offset position 128 of the adapter plate 80 previously used was not appropriate. Such reiterative steps are performed until a satisfactory offset position 128 is found. Similarly, the method may include repeating the steps of placing the glenoid trial 30 over the adapter plate 80, moving the humeral cup 34 into contact with the glenoid trial 30, and moving the humerus 22 through a range of motion with glenoid trials 30 of varying sizes in response to determining that the glenoid trial 30 previously used was not of appropriate size. Again, these reiterative steps are performed until a satisfactory glenoid trial size is found.

The method additionally includes the steps of separating the adapter assembly 28 and the glenoid baseplate component 44 by removing the body portion 86 of the adapter 78 from the primary bore 64 of the glenoid baseplate component 44 and installing a glenoid implant 32 on the adapter plate 80 of the adapter assembly 28. As discussed above, the step of installing the glenoid implant 32 may further include pressing the glenoid implant 32 onto the adapter plate 80 of the adapter assembly 28. The method also includes re-inserting the body portion 86 of the adapter 78 into the primary bore 64 of the glenoid baseplate component 44. This step of re-inserting the body portion 86 of the adapter 78 into the primary bore 64 may include re-inserting the locking projection 98 of the adapter 78 into the rotation interface 74 of the primary fastener 46 to lock rotation of the adapter 78 relative to the primary fastener 46 and the glenoid baseplate component 44 and pressing the body portion 86 of the adapter 78 into the primary bore 64 of the glenoid baseplate component 44 to create a press fit between the body portion 86 and the glenoid baseplate component 44. As a result of the press fit created during this step, the adapter assembly 28 and the glenoid baseplate component 44 are prevented from separating post-surgery. The method further includes the step of moving the humeral cup 34 into contact with the glenoid implant 32. It should be appreciated that the order of the steps recited herein is exemplary in nature and is not intended to be limiting. Furthermore, it is envisioned that a variety of additional steps may be performed during surgery, either before, after, or during the method set forth above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. These antecedent recitations should be interpreted to cover any combination in which the inventive novelty exercises its utility. Many modifications and variations of the present invention are possible in light of the above teachings and may be practiced otherwise than as specifically described while within the scope of the appended claims.

What is claimed is:

1. A glenoid trial and implant assembly for reverse total shoulder arthroplasty comprising:
    a glenoid baseplate component including a primary bore, wherein said glenoid baseplate component is configured for fixation to a glenoid;
    an adapter assembly including an adapter, said adapter including an adapter flange and a body portion extending from said adapter flange, wherein said body portion is received in said primary bore of said glenoid baseplate component;
    a glenoid trial presenting a lateral glenoid trial face that has a bulbus shape and a medial glenoid trial face that defines a glenoid trial cavity, wherein said glenoid trial is coupled to said adapter assembly when said glenoid trial and implant assembly is in a trialing configuration;
    a glenoid implant presenting a lateral glenoid implant face that has a bulbus shape and a medial glenoid implant face that defines a glenoid implant cavity, wherein said bulbus shape of said lateral glenoid implant face matches said bulbus shape of said lateral glenoid trial face, and wherein said glenoid implant is coupled to said adapter assembly when said glenoid trial and implant assembly is in an installed configuration;
    a humeral cup presenting a concave surface, wherein said concave surface of said humeral cup abuts said lateral glenoid trial face when said glenoid trial and implant assembly is in said trialing configuration, and wherein said concave surface of said humeral cup abuts said lateral glenoid implant face when said glenoid trial and implant assembly is in said installed configuration;
    said adapter assembly including an adapter plate coupled to said adapter, said adapter plate abutting said adapter flange, wherein said adapter plate and said adapter are discrete components, wherein said adapter plate is received in said glenoid trial cavity when said glenoid trial and implant assembly is in said trialing configuration, and wherein said adapter plate is received in said glenoid implant cavity when said glenoid trial and implant assembly is in said installed configuration;
a temporary connection releasably coupling said glenoid trial to said adapter assembly that provides separation of said glenoid trial and said adapter assembly without requiring disassembly of said adapter assembly; and
a permanent connection fixedly coupling said glenoid implant to said adapter assembly.

2. A glenoid trial and implant assembly as set forth in claim 1, wherein said temporary connection is a magnetic connection between said glenoid trial and said adapter assembly.

3. A glenoid trial and implant assembly as set forth in claim 2, wherein said magnetic connection includes at least one of an adapter plate magnet that is carried on said adapter plate and a glenoid trial magnet that is carried on said glenoid trial.

4. A glenoid trial and implant assembly as set forth in claim 2, wherein said magnetic connection includes at least one adapter plate magnet carried on said adapter plate and at least one glenoid trial magnet carried on said glenoid trial.

5. A glenoid trial and implant assembly as set forth in claim 1, wherein said permanent connection includes a press fit between said adapter plate and said glenoid implant, said adapter plate and said glenoid implant each including complementary tapers such that said adapter plate becomes fixed to said glenoid implant when said adapter assembly is pressed into said glenoid implant cavity.

6. A glenoid trial and implant assembly as set forth in claim 1, further comprising:
a positioning guide including a hub and a positioning guide flange that extends outwardly from said hub, said hub defining a hub cavity that receives said adapter plate and said positioning guide flange having a plurality of annular rings each representing different glenoid trial sizes.

7. A glenoid trial and implant assembly as set forth in claim 6, wherein said positioning guide is magnetically retained on said adapter plate.

8. A glenoid trial and implant assembly as set forth in claim 1, wherein said adapter assembly includes an adapter fastener coupling said adapter plate to said adapter, said adapter fastener including an adapter fastener head that tightens against said adapter plate and that is entirely covered by said glenoid trial when said glenoid trial and implant assembly is in said trialing configuration.

9. A glenoid trial and implant assembly for reverse total shoulder arthroplasty comprising:
a glenoid baseplate component configured to be surgically coupled to the glenoid, said glenoid baseplate component including a primary bore;
an adapter assembly including an adapter, said adapter having a body portion that is received in said primary bore of said glenoid baseplate component;
a glenoid trial presenting a lateral glenoid trial face that has a bulbus shape and a medial glenoid trial face that defines a glenoid trial cavity, wherein said glenoid trial is coupled to said adapter assembly when said glenoid trial and implant assembly is in the trialing configuration;
a glenoid implant presenting a lateral glenoid implant face that has a bulbus shape and a medial glenoid implant face that defines a glenoid implant cavity, wherein said bulbus shape of said lateral glenoid implant face matches said bulbus shape of said lateral glenoid trial face, and wherein said glenoid implant is coupled to said adapter assembly when said glenoid trial and implant assembly is in the installed configuration;
a humeral cup presenting a concave surface, wherein said concave surface of said humeral cup abuts said lateral glenoid trial face when said glenoid trial and implant assembly is in the trialing configuration, wherein said concave surface of said humeral cup abuts said lateral glenoid implant face when said glenoid trial and implant assembly is in the installed configuration, and wherein said humeral cup is configured to be surgically coupled to the humerus;
said adapter assembly including an adapter plate, wherein said adapter plate is received in said glenoid trial cavity when said glenoid trial and implant assembly is in the trialing configuration, and wherein said adapter plate is received in said glenoid implant cavity when said glenoid trial and implant assembly is in the installed configuration;
a magnetic connection releasably coupling said glenoid trial to said adapter assembly; and
a permanent connection fixedly coupling said glenoid implant to said adapter assembly.

10. A glenoid trial and implant assembly for reverse total shoulder arthroplasty where said glenoid trial and implant assembly is disposed between a humerus and a glenoid of a human body, said glenoid trial and implant assembly comprising:
a baseplate assembly including a glenoid baseplate component and a primary fastener;
said glenoid baseplate component including a primary bore that extends through said glenoid baseplate component;
said primary fastener extending through said primary bore and projecting from said glenoid baseplate component to fix said glenoid baseplate component to the glenoid;
said primary fastener having a primary fastener head presenting a rotation interface;
an adapter assembly including an adapter and an adapter plate;
said adapter including an adapter bore, an adapter flange, and a body portion extending from said adapter flange to a medial body portion end, wherein said body portion is received in said primary bore of said glenoid baseplate component;
a glenoid trial presenting a lateral glenoid trial face that has a bulbus shape and a medial glenoid trial face that defines a glenoid trial cavity, wherein said glenoid trial is coupled to said adapter assembly when said glenoid trial and implant assembly is in a trialing configuration;
a glenoid implant presenting a lateral glenoid implant face that has a bulbus shape and a medial glenoid implant face that defines a glenoid implant cavity, wherein said bulbus shape of said lateral glenoid implant face matches said bulbus shape of said lateral glenoid trial face, and wherein said glenoid implant is coupled to said adapter assembly when said glenoid trial and implant assembly is in an installed configuration;
a humeral cup presenting a concave surface, wherein said concave surface of said concave cup abuts said lateral glenoid trial face when said glenoid trial and implant assembly is in said trialing configuration, wherein said concave surface of said humeral cup abuts said lateral glenoid implant face when said glenoid trial and implant assembly is in said installed configuration, and wherein said humeral cup is configured to couple to the humerus;

said adapter plate of said adapter assembly abutting said adapter flange, wherein said adapter plate is received in said glenoid trial cavity when said glenoid trial and implant assembly is in said trialing configuration, and wherein said adapter plate is received in said glenoid implant cavity when said glenoid trial and implant assembly is in said installed configuration; and said adapter including a locking projection extending from said medial body portion end that is received in and engages said rotation interface of said primary fastener to prevent rotation of said adapter relative to said primary fastener and said glenoid baseplate component when said glenoid trial and implant assembly is in said trialing configuration and when said glenoid trial and implant assembly is in said installed configuration.

11. A glenoid trial and implant assembly as set forth in claim 10, wherein said locking projection of said adapter and said rotation interface of said primary fastener each have a hexagonal shape.

12. A glenoid trial and implant assembly as set forth in claim 10, wherein said adapter plate is coupled to said adapter and wherein said adapter plate and said adapter are discrete components of said adapter assembly.

13. A glenoid trial and implant assembly as set forth in claim 12, wherein said adapter includes a lateral adapter plate face and a medial adapter plate face and wherein said lateral adapter plate face is disposed within said glenoid trial cavity adjacent said medial glenoid trial face when said glenoid trial and implant assembly is in said trialing configuration and is disposed in said glenoid implant cavity adjacent said medial glenoid implant face when said glenoid trial and implant assembly is in said installed configuration.

14. A glenoid trial and implant assembly as set forth in claim 13, wherein said medial adapter plate face defines a medial adapter plate cavity that receives said adapter flange and wherein said medial adapter plate cavity is larger than said adapter flange and is elongated along an offset direction such that said adapter may be shifted relative to said adapter plate in said offset direction when said glenoid trial and implant assembly is in said trialing configuration.

15. A glenoid trial and implant assembly as set forth in claim 14, wherein said adapter plate includes a pass-through that extends between and that is open to said lateral adapter plate face and said medial adapter plate cavity.

16. A glenoid trial and implant assembly as set forth in claim 15, wherein said adapter assembly includes an adapter fastener that extends through said pass-through and into said adapter bore to selectively fix said adapter plate to said adapter and wherein said pass-through is elongated along said offset direction such that said adapter may be shifted relative to said adapter plate in said offset direction when said glenoid trial and implant assembly is in said trialing configuration, said adapter fastener having an adapter fastener head that tightens against said adapter plate to fix said adapter plate in place relative to said adapter at an offset position located along said offset direction.

17. A glenoid trial and implant assembly as set forth in claim 16, further comprising:

a temporary connection releasably coupling said glenoid trial to said adapter assembly that provides separation of said glenoid trial and said adapter assembly while maintaining said offset position of said adapter plate relative to said adapter and without requiring disassembly of said adapter assembly.

18. A glenoid trial and implant assembly as set forth in claim 17, wherein said temporary connection is a magnetic connection between said glenoid trial and said adapter assembly.

19. A glenoid trial and implant assembly as set forth in claim 16, wherein said adapter includes a pin bore extending into said adapter bore, wherein said adapter fastener includes a first stop that is spaced from said adapter fastener head and a second stop that is spaced from said first stop, said first and second stops extending outwardly from said adapter fastener, and wherein said adapter assembly includes a pin that is received in said pin bore that limits axial movement of said adapter fastener within said adapter bore by contacting said first and second stops of said adapter fastener.

* * * * *